United States Patent
Hwang et al.

(10) Patent No.: US 11,607,674 B2
(45) Date of Patent: Mar. 21, 2023

(54) HETEROGENEOUS CATALYST COMPLEX FOR CARBON DIOXIDE CONVERSION

(71) Applicant: KOREA RESEARCH INSTITUTE OF CHEMICAL TECHNOLOGY, Daejeon (KR)

(72) Inventors: Young Kyu Hwang, Daejeon (KR); Jaesung Kwak, Daejeon (KR); Maeum Lee, Daejeon (KR); Anil Haribhau Valekar, Daejeon (KR); Kyung Ryul Oh, Daejeon (KR); Do Young Hong, Daejeon (KR); A Reum Byeun, Daejeon (KR); Dong Won Hwang, Daejeon (KR); Joungmo Cho, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 17/097,454

(22) Filed: Nov. 13, 2020

(65) Prior Publication Data

US 2021/0146344 A1 May 20, 2021

(30) Foreign Application Priority Data

Nov. 19, 2019 (KR) .................. 10-2019-0148958
Sep. 29, 2020 (KR) .................. 10-2020-0127356

(51) Int. Cl.
*C07C 51/09* (2006.01)
*B01J 23/89* (2006.01)
*B01J 23/46* (2006.01)
*C07C 67/40* (2006.01)

(52) U.S. Cl.
CPC ......... *B01J 23/8913* (2013.01); *B01J 23/462* (2013.01); *C07C 51/09* (2013.01); *C07C 67/40* (2013.01)

(58) Field of Classification Search
CPC ......... C07C 51/09; C07C 51/15; C07C 53/02; C07C 67/40; C07C 51/295; C07C 53/06; C07C 59/08; B01J 23/462; B01J 23/8913; B01J 21/18; B01J 23/06; B01J 23/60; B01J 35/0013; B01J 35/002; B01J 37/033; B01J 37/082; B01J 37/088
See application file for complete search history.

(56) References Cited

FOREIGN PATENT DOCUMENTS

| CN | 107118092 | * | 9/2017 | |
|----|-----------|---|--------|---|
| KR | 10-1140649 B1 | | 5/2012 | |
| KR | 10-1198866 B1 | | 11/2012 | |
| KR | 10-2014-0033491 A | | 3/2014 | |
| KR | 10-1515981 B1 | | 4/2015 | |
| KR | 10-2019-0063662 A | | 6/2019 | |
| WO | WO-2018213821 A1 | * | 11/2018 | ............ B01J 21/16 |

OTHER PUBLICATIONS

CN 107118092 translated (Year: 2017).*
Jacob Heltzel et al., "Transfer Hydrogenation of Carbon Dioxide and Bicarbonate from Glycerol Under Aqueous Conditions", Chem. Commun., 2018, DOI: 10.1039/C8CC03157F.
Office Action dated Feb. 2, 2023, for corresponding Korean Patent Application No. 10-2019-0148958, along with an English machine translation (17 pages).
Ji Su et al., "Simultaneously Converting Carbonate/Bicarbonate and Biomass to Value-added Carboxylic Acid Salts by Aqueous-phase Hydrogen Transfer", Sustainable Chemistry & Engineering, Dec. 8, 2014, vol. 3, pp. 195-203.

* cited by examiner

*Primary Examiner* — Yevgeny Valenrod
*Assistant Examiner* — Blaine G Doletski
(74) *Attorney, Agent, or Firm* — Hauptman Ham, LLP (57) ABSTRACT

Proposed is a catalyst complex having high activity for carbon dioxide conversion reaction that converts carbon dioxide to useful compounds through reaction of carbon dioxide and hydrocarbon containing at least one hydroxyl group, and a carbon dioxide conversion process using the same, wherein the catalyst complex includes, as an active metal in the catalyst complex, at least one of noble metals and at least one of transition metals other than noble metals, thereby having high activity for the carbon dioxide conversion reaction.

16 Claims, 5 Drawing Sheets

HETEROGENEOUS CATALYST COMPLEX FOR CARBON DIOXIDE CONVERSION

CROSS REFERENCE TO RELATED APPLICATION

The present application claims priority based on Korean Patent Application No. 10-2020-0127356, filed on Sep. 29, 2020 and Korean Patent Application No. 10-2019-0148958, filed on Nov. 19, 2019, the entire content of which is incorporated herein for all purposes by this reference.

BACKGROUND OF THE DISCLOSURE

1. Technical Field

The present disclosure generally relates to a catalyst complex for carbon dioxide conversion reaction that converts carbon dioxide into useful compounds. More particularly, the present disclosure relates to a catalyst that promotes the production of useful compounds by reacting carbon dioxide and/or carbon dioxide-derived inorganic carbonate with hydrocarbon containing at least one hydroxy functional group in molecules, and also relates to a carbon dioxide conversion reaction system using the same.

2. Description of the Related Art

Coal and oil, which are fossil energy resources that account for 50% of all energy resources have served as primary energy resources for mankind for the last centuries, and the mankind have emitted, without a separate post-treatment process, carbon dioxide generated from the use of these fossil energy resources, but due to the effect of carbon dioxide as a greenhouse gas, efforts have been made to capture carbon dioxide and convert the carbon dioxide into other useful compounds.

However, carbon dioxide is a carbon compound having fairly low energy that takes a great deal of energy to be converted into a useful resource, which serves as a stumbling block that prevents carbon dioxide conversion technology from becoming a commercial success. In this regard, if a catalyst that minimizes energy use and enhances reaction selectivity is developed, the carbon dioxide conversion technology will be able to not only treat carbon dioxide but also re-convert carbon dioxide into a useful material at an affordable cost to create added value, and is therefore considered to become a highly useful technology.

One of carbon dioxide conversion processes is a process for converting carbon dioxide to formic acid through hydrogenation, and may be specifically represented by Scheme 1 below.

(Scheme 1)

$\Delta G°\ aq\ (kcal/mol) = 13.4$

As a related art, Korean Patent Application Publication No. 2014-0033491 discloses a method of preparing formic acid, using a heterogeneous catalyst using, as a support, silicon dioxide, aluminum oxide, zirconium oxide, magnesium oxide, etc., and containing gold therein, but the method has unsatisfactory catalyst efficiency, and adopts a process of directly hydrogenating carbon dioxide using hydrogen. Thus, the related art method has a high $\Delta G$ value of 13.4 as shown in Scheme 1 above, so that a great deal of energy resources are required to perform reaction.

However, the reaction of preparing formic acid by reacting hydrocarbon, such as glycerol, containing at least one hydroxyl group with carbon dioxide has a low $\Delta G$ value, and the reaction may thus be thermodynamically performed relatively much easier than a reaction of using hydrogen directly. Therefore, if an innovative catalyst is developed for the reaction, it is expected that the development will become an energy-saving carbon dioxide conversion technology.

Hydrocarbon containing at least one hydroxyl group may be one selected glucose, mannose, galactose, xylose, sorbitol, mannitol, galactitol, xylitol, glycerol, 1,4-butanediol or an isomer thereof, 1,4-pentanediol or an isomer thereof, 1,2-propane diol or an isomer thereof, butanol, pentanol, and propanol, or a mixture thereof.

In particular, glycerol is generated as a by-product in the production process of biodiesel and is currently simply incinerated as a waste, thereby generating a large amount of carbon dioxide during the incineration process of such a by-product to cause an emerging issue of secondary environmental pollution. Accordingly, research on how to utilize glycerol produced as a by-product in the production process of biodiesel is being conducted together, and carbon dioxide conversion, through which formic acid and lactic acid are produced from the reaction of carbon dioxide and glycerol, may be a good solution to resolve the issues of glycerol treatment and carbon dioxide conversion together.

The process of obtaining formic acid and lactic acid from the reaction of glycerol and carbon dioxide may be represented by Scheme 2 below.

Recently, a homogeneous organometallic catalyst (Ru—N-heterocyclic carbene) that promotes the reaction of producing lactic acid and formic acid from the reaction of glycerol and carbon dioxide has been developed (Non-Patent Document 1).

(Scheme 2)

$\Delta G°_{aq}\ (kcal/mol) = -9.21$

However, the homogeneous catalyst has a problem in that the catalyst must be separated from a reaction product mixture. On the contrary, a heterogeneous catalyst is advantageous in that a high-purity product can be obtained because of absence of residues derived from homogeneous catalysts as well as convenience in process.

Therefore, using a heterogeneous catalyst complex as a catalyst for carbon dioxide conversion reaction improves process efficiency and is an eco-friendly technology that enables recycling, thus having a great value in research. To this end, there is a demand for the development of a heterogeneous catalyst capable of converting carbon dioxide stably with high activity.

Meanwhile, the product obtained through Scheme 2 is present in the form of a formic acid metal salt and a metal lactic acid salt, and in order to separate and recover the generated formic acid metal salt and lactic acid metal salt with high purity, there may be a method of converting the generated salts to an organic compound having a boiling point through esterification with alcohol, and then performing separation through distillation, etc.

As a related art, Korean Patent Application Publication No. 2019-0063662 (published on Jun. 10, 2019) discloses a method in which the temperature of a culture solution containing lactate is lowered to form lactate crystals, and the resultant is then filtered and separated to remove water, and Korean Patent No. 1198866 (registered on Nov. 1, 2012) and No. 1515981 (registered on Apr. 22, 2015) disclose a method in which an appropriate amount of moisture is removed prior to addition of alcohol, and the alcohol and an acid solution are added to perform an esterification reaction.

In addition, Korean Patent No. 1140649 (registered on Apr. 20, 2012) discloses a method involving a first-stage process of producing a lactic acid using a trialkyl phosphate extracting agent without performing a pre-treatment process using sulfuric acid, etc., and a second-stage process of adding alcohol to the obtained lactic acid to perform an esterification reaction thereby preparing a lactic acid derivative having a short chain alkyl group bonded thereto, wherein the first-stage process is performed under the moisture removal condition to increase yield in the second-stage reaction.

However, the relate art methods described above still require repeating a process due to a low yield, thereby causing high cost for the process. Therefore, a process technology for effectively removing metal atoms from organic acid metal salts and increasing the yield of the esterification reaction is needed.

SUMMARY OF THE DISCLOSURE

In order to overcome the problems described above, the present researchers have completed the present disclosure while researching and developing a catalyst complex for reaction of carbon dioxide and hydrocarbon containing at least one hydroxyl group.

Accordingly, the present disclosure has been made keeping in mind the above problems occurring in the related art, and the present disclosure is intended to provide, as a catalyst for converting carbon dioxide to a useful compound by reacting at least one among carbon dioxide and inorganic carbonate with hydrocarbon containing at least one hydroxyl group, a catalyst complex in which two or more kinds of metals as an active metal are supported on a support.

Also, the present disclosure is intended to provide an efficient carbon dioxide conversion process of converting carbon dioxide to a useful compound by reacting at least one among carbon dioxide and inorganic carbonate with hydrocarbon containing at least one hydroxyl group.

An aspect of the present disclosure provides a method of converting carbon dioxide to formic acid, wherein the method includes reacting at least one among carbon dioxide and/or carbon dioxide-derived inorganic carbonates with hydrocarbon containing at least one hydroxyl group in the presence of a catalyst in which, as an active metal in a catalyst complex, at least one of noble metals and at least one selected from among transition metals other than the noble metal are supported on a support.

According to an embodiment of the present disclosure, the noble metals may be at least one selected from among ruthenium (Ru), iridium (Ir), rhodium (Rh), platinum (Pt), palladium (Pd), and gold (Au), and the transition metals other than the noble metals may be at least one selected from among zinc (Zn), nickel (Ni), iron (Fe), cobalt (Co), manganese (Mn), magnesium (Mg), aluminum (Al), titanium (Ti), chromium (Cr), copper (Cu), zirconium (Zr), molybdenum (Mo), indium (In), barium (Ba), hafnium (Hf), and cerium (Ce).

According to another embodiment of the present disclosure, the support may be at least one selected from among a carbonaceous material, a molecular sieve, a ceramic material, and a metal oxide, and the hydrocarbon containing at least one hydroxyl group may be one selected from among a monohydric alcohol and a polyhydric alcohol, or a mixture thereof.

The hydrocarbon containing at least one hydroxyl group may be one selected from among glucose, mannose, galactose, xylose, sorbitol, mannitol, galactitol, xylitol, glycerol, 1,4-butanediol or an isomer thereof, 1,4-pentanediol or an isomer thereof, 1,2-propanediol or an isomer thereof, butanol, pentanol, and propanol, or a mixture thereof, preferably glycerol and/or glucose.

According to an embodiment of the present disclosure, the temperature of the carbon dioxide conversion reaction may be 180° C. to 240° C., and the inorganic carbonate may be $NaHCO_3$ or $KHCO_3$.

In addition, the method of converting carbon dioxide to formic acid may further include, before reacting hydrocarbon containing at least one hydroxyl group with inorganic carbonate, reacting carbon dioxide with at least one selected from among a metal, a metal salt, and an ammonium salt to produce an inorganic carbonate.

The present disclosure also provides a method of preparing a compound through dehydrogenation in a hydroxyl group from the hydrocarbon containing at least one hydroxyl group through reaction of at least one among carbon dioxide and/or inorganic carbonate with hydrocarbon containing at least one hydroxyl group.

According to another embodiment of the present disclosure, there is provided a process for simultaneously converting a carbon dioxide-derived metal carbonate and glycerol, the process including a) performing, in the presence of a catalyst complex for carbon dioxide conversion reaction, a simultaneous conversion reaction of a carbon dioxide-derived metal carbonate and glycerol to obtain a reaction product, b) forming a mixture in which at least one selected from among $C_4$ to $C_8$ alcohols and trialkyl phosphate (TAP) are added to the obtained reaction product, c) removing some moisture from the mixed solution, d) performing carbonation and esterification by adding carbon dioxide ($CO_2$) to the mixed solution from which some moisture is removed, and performing an esterification reaction to synthesize alkyl lactate and alkyl formate, e) separating the alkyl lactate and the alkyl formate produced in step d) from each other through conventional methods such as distillation, and f) recovering the metal carbonate produced as a reaction by-product in step d), and recycling the metal carbonate to the simultaneous conversion reaction of glycerol and metal carbonate, wherein the catalyst complex is a catalyst in which at least one of noble metals and at least one selected from among transition metals other than the noble metals are supported as an active metal on a support.

According to another embodiment of the present disclosure, the amount of alcohol added in step b) is 1 to 50 in a ratio of the number of moles to the sum of the number of moles of metal lactate and metal formate, and the molar ratio of the alcohol to trialkyl phosphate (TBP) is 1:5 to 5:1, and at least one alcohol selected from among $C_4$ to $C_8$ added in step b) may be butanol, and an inert organic solvent may be tributyl phosphate (TBP). In addition, the carbon dioxide added in step d) is supplied while being pressurized in a range of atmospheric pressure to 60 bar.

According to another embodiment of the present disclosure, the carbonation and esterification processes in step d) are performed in a temperature range of 120° C. to 200° C.

According to another embodiment of the present disclosure, the process may further include g) hydrolyzing the alkyl lactate and the alkyl formate to produce a lactic acid and a formic acid.

According to another embodiment of the present disclosure, the trialkyl phosphate (TAP) may be added in step d) after the removing of moisture, instead of being added in step b).

A catalyst complex according to the present disclosure can produce formic acid and formic acid derivatives in high yield even at relatively low temperatures from carbon dioxide conversion reaction of carbon dioxide or inorganic carbonate.

In addition, the catalyst complex according to the present disclosure can be used as a heterogeneous catalyst to be easily separated from a reaction product, and after being used as a catalyst, the catalyst can be recovered and used repeatedly.

Further, a carbon dioxide conversion system according to the present disclosure is capable of converting carbon dioxide to useful compounds with high efficiency.

DESCRIPTION OF SPECIFIC EMBODIMENTS

Hereinafter, exemplary embodiments of the present disclosure that can be easily practiced by those having ordinary skill in the technical field to which the present disclosure pertains will be described in detail. In describing operations of the exemplary embodiments in detail, when it is determined that the specific description of related well-known functions or constitutions unnecessarily obscures the gist of the present disclosure, the detailed description thereof will be omitted.

The present disclosure relates to a catalyst complex for a carbon dioxide conversion reaction, wherein the carbon dioxide conversion reaction refers to a reaction of at least one among carbon dioxide and inorganic carbonate with hydrocarbon containing at least one hydroxyl group, and the catalyst complex has at least two types of active metals supported on a support.

The active metals may include at least one of noble metals, and at least one selected from among other transition metals may be supported on a support.

As an active metal component in the catalyst complex, the noble metal is preferably at least one selected from among ruthenium (Ru), iridium (Ir), rhodium (Rh), platinum (Pt), palladium (Pd), and gold (Au), and more preferably ruthenium (Ru), platinum (Pt), and palladium (Pd).

A ruthenium compound as a precursor of the ruthenium (Ru) may be, although not limited to, for example, ruthenium salts such as $RuCl_3 \cdot nH_2O$, $Ru(NO_3)_3$, $Ru_2(OH)_2Cl_4 \cdot 7NH_3 \cdot 3H_2O$, $K_2(RuCl_5(H_2O))$, $(NH_4)_2(RuCl_5(H_2O))$, $K_2(RuCl_5(NO))$, $RuBr_3 \cdot nH_2O$, $Na_2RuO_4$, $Ru(NO)(NO_3)_3$, $Ru_3(CO)_{12}$, $[Ru_3O(OAc)_6 (ligand)_3][X]$, (ligand=$H_2O$, alcohol, amine, X=anion) $Ru(acac)_3$, $[Ru(p-cymene) Cl_2]_2$, etc., and preferably one selected from the group consisting of $Ru(NO)(NO_3)_3$ and $Ru(NO_3)_3$ in terms of handling.

A iridium compound as a precursor of the iridium may be one selected from the group consisting of $(NH_4)_2IrCl_6$, $IrCl_3$ or $H_2IrCl_6$, $Ir(acac)_3$, $[Ir (cod) Cl]_2$, $[Ir (coe)_2Cl]_2$, $Ir_4(CO)_{12}$, $[Ir_3O(OAc)_6(ligand)_3][X]$ (ligand=$H_2O$, alcohol, amine, X=anion), and $[IrCp*Cl_2]_2$, but is not limited thereto.

A rhodium compound as a precursor of the rhodium (Rh) may be one selected from the group consisting of $Na_3RhCl_6$, $(NH_4)_2RhCl_6$, $Rh(NH_3)_5Cl_3$, $RhCl_3$, $Rh(acac)_3$, $[Rh(cod)Cl]_2$, $[Rh(coe)_2Cl]_2$, $Rh_4(CO)_{12}$, $[Rh_3O(OAc)_6 (ligand)_3][X]$ (ligand=$H_2O$, alcohol, amine, X=anion), $Rh_2(OAc)_4$, and $[RhCp*Cl_2]_2$, but is not limited thereto.

A platinum compound as a precursor of the platinum (Pt) may be, for example, one selected from the group consisting of $PtCl_4$, $H_2PtCl_4$, $H_2PtCl_6$, $K_2PtCl_4$, $K_2PtCl_6$, $Pt(C_5H_7O_2)_2$, and $Pt(acac)_2$, but is not limited thereto.

A palladium compound as a precursor of the palladium (Pd) may be one selected from the group consisting of $(NH_4)_2PdCl_6$, $(NH_4)_2PdCl_4$, $Pd(NH_3)_4Cl_2$, $PdCl_2$, $Pd(NO_3)_2$, $Pd(OAc)_2$, and $Pd(acac)_2$, but is not limited thereto.

A gold compound as a precursor if the gold (Au) may be one selected from the group consisting of $HAuCl_4$, $AuCl_3$, $NaAuCl_4$, $KAuO_2$, $NaAuO_2$, $Au(OAc)_3$, and $HAu(NO_3)_4$, but is not limited thereto.

In addition, as an active metal component in the catalyst complex, metals other than noble metals preferably include at least one selected from among zinc (Zn), nickel (Ni), iron (Fe), cobalt (Co), manganese (Mn), magnesium (Mg), and aluminum (Al), titanium (Ti), chromium (Cr), copper (Cu), zirconium (Zr), molybdenum (Mo), indium (In), barium (Ba), hafnium (Hf) and cerium (Ce).

The catalyst according to the present disclosure may be used only with an active metal, but is generally used by being supported on a support. The support, which is a solid that stably holds a material having a catalytic function through dispersion, indicates a material that is highly dispersed and held so as to increase an exposed surface area of the material having a catalytic function, and a material that is usually porous or has a large area, and is mechanically, thermally, and chemically stable. The support is selected in consideration of the diameter, volume, surface area, strength, chemical stability, and shape of pores in the support. Since the catalytic activity may vary with types of a support, the support may be properly selected suitable for the type of an active metal and the type of applied reaction.

The support according to the present disclosure may include activated carbon, carbonaceous materials such as graphite carbon, molecular sieves such as zeolite and metal-organic framework (MOF), ceramic materials such as hydrotalcite, perovskite, spinel (e.g., $CoAl_2O_4$), metal oxides such as alumina and silica, sulfate-treated metal oxides (e.g., $ZrO_2$—$SO_4$, $SnO_2$—$SO_4$), and metal oxyhydroxides (e.g., AlOOH, $ZrO(OH)_2$, COOH), and preferably include graphite carbon.

The support may be commercially available, or manufactured and used. For example, a graphite carbon body, as a support in a catalyst complex, may use a metal organic framework as a starting material, and use a graphite phase formed by being fired at high temperature.

In order to prepare the catalyst complex according to the present disclosure, known methods in the technical field to which the present disclosure pertains, such as impregnation, coprecipitation, solid support, vapor deposition, wash coat, sol-gel, and in-situ synthesis, may be used to support the active metal.

For example, supporting through impregnation includes immersing a support in a precursor solution of an active metal and drying the support immersed in the noble metal precursor solution.

The precursor solution may be prepared using any known solvent capable of dissolving the precursor, for example, water, glycol-based solvents such as ethylene glycol, 1,2-propylene glycol, 1,3-butanediol, 1,4-butanediol, neopentyl glycol, diethylene glycol, 3-methyl-1,5-pentanediol, 1,6-hexanediol, and trimethylolpropane, or alcohol-based solvents such as methanol, ethanol, isopropyl alcohol (IPA), and butanol.

In addition, the active metal-supported support is preferably fired at 500° C. to 1100° C. for 3 to 12 hours to prepare a catalyst complex.

According to a preferred embodiment of the present disclosure, it is preferable that the amount of the active metal contained in a complex catalyst system for carbon dioxide conversion reaction is 0.1 wt % to 50 wt %.

According to the present disclosure, when the amount of the active metal is less than 0.1 wt %, active elements in the carbon dioxide conversion reaction are not sufficiently present to cause a decrease in reactivity. Meanwhile, when the amount of the active metal is greater than 50 wt %, the activity decreases due to an increase in the particle size of the active metal, thereby causing severer caulking, and it is thus preferable to keep the above range.

In addition, the noble metals and the transition metals other than the noble metals may be supported at a molar ratio of 1:1 to 1:200, preferably at a molar ratio 1:10 to 1:100.

In the carbon dioxide conversion reaction, the hydrocarbon containing at least one hydroxyl group may be one selected from among a monohydric alcohol and a polyhydric alcohol, or a mixture thereof. It is preferable, in terms of reactivity with carbon dioxide, that the hydrocarbon containing at least one hydroxyl group is glucose, mannose, galactose, xylose, sorbitol, mannitol, galactitol, xylitol, glycerol, 1,4-butanediol or an isomer thereof, 1,4-pentanediol or an isomer thereof, 1,2-propanediol or an isomer thereof, butanol, pentanol, and a mixture thereof. It is more preferable, in terms of the environment aspects and raw material supply, that the hydrocarbon containing at least one hydroxyl group is glucose, xylose, and glycerol.

In addition, in the carbon dioxide conversion reaction, the carbon dioxide may be in the form of a carbon dioxide molecule or carbon dioxide-derived carbonate. The carbon dioxide-derived carbonate is an inorganic carbonate produced when carbon dioxide combines with a metal, ammonium or the like, and may be preferably a metal carbonate or metal bicarbonate compound.

The inorganic carbonate, produced through combination of carbon dioxide with metal or ammonium ions, may be at least one selected from among, for example, $MgCO_3$, $Mg(CO_3)_2$, $CaCO_3$, $KHCCO_3$, $K_2CO_3$, $NaHCO_3$, $Na_2CO_3$, $LiHCO_3$, $Li_2CO_3$, $FeCO_3$, $CuCO_3$, $Ag_2CO_3$, $BaCO_3$, $SrCO_3$, $MnCO_3$, $Mn(CO_3)_2$, $KHCO_3$, $NaHCO_3$, $(NH_4)_2CO_3$, $NH_4HCO_3$, $RbHCO_3$, $Rb_2CO_3$, $CsHCO_3$ and $Cs_2CO_3$, and more preferably, $KHCO_3$, $K_2CO_3$, $NaHCO_3$, $Na_2CO_3$, $LiHCO_3$, $Li_2CO_3$, $(NH_4)_2CO_3$, $NH_4HCO_3$, $RbHCO_3$, $Rb_2CO_3$, $CsHCO_3$ and $Cs_2CO_3$.

The carbon dioxide conversion reaction of the present disclosure may further include, before reacting hydrocarbon containing at least one hydroxyl group with carbon dioxide or inorganic carbonate, reacting carbon dioxide with a metal or a metal salt to produce an inorganic carbonate.

In the carbon dioxide conversion reaction of the present disclosure, it can be seen that when carbon dioxide is in the form of carbonate rather than molecular carbon dioxide, the ΔG value of reaction becomes lower, and the reaction is more likely to be triggered.

For example, in the carbon dioxide conversion reaction, when the hydrocarbon containing at least one hydroxyl group is glycerol, the carbon dioxide conversion reaction may be a reaction of carbon dioxide and glycerol represented by Scheme 2 and/or a reaction of inorganic carbonate and glycerol represented by Scheme 3.

(Scheme 2)

(Scheme 3)

Table 1 below shows ΔG values of the conversion reaction of hydrocarbon containing at least one hydroxyl group and carbon dioxide according to the present disclosure.

TABLE 1

| Substrates | Products | Source of alcohol | ΔG (kcal/mol) |
| --- | --- | --- | --- |
| Ethanol + NaHCO3 (or CO2) | Acetaldehyde + Formic acid | Biomass derived sugar fermentation | 5.24 (7.94) |
| Butanol + NaHCO3 (or CO2) | Butanone + Formic acid | Biomass derived sugar fermentation | 5.76 (8.47) |
| Glucose + NaHCO3 (or CO2) | Gluconic acid, Sorbitol + Formic acid | Hydrolysis of cellulose | −14.34 (−11.64) |
| Mannose + NaHCO3 (or CO2) | Mannaric acid, Mannitol + Formic acid | Hydrolysis of cellulose | −3.14 (−0.44) |
| Galactose + NaHCO3 (or CO2) | Galactonic acid, Galactitol + Formic acid | Hydrolysis of hemicellulose | −9.55 (−6.84) |
| Xylose + NaHCO3 (or CO2) | Xylonic acid, Xylitol + Formic acid | Hydrolysis of hemicellulose | −16.27 (−13.56) |

TABLE 1-continued

| Substrates | Products | Source of alcohol | ΔG (kcal/mol) |
|---|---|---|---|
| Sorbitol + NaHCO3 (or CO2) | Lactic acid + Formic acid | Hydrogenation of glucose | −42.48 (−39.78) |
| Mannitol + NaHCO3 (or CO2) | Lactic acid + Formic acid | Hydrogenation of mannose | −40.40 (−37.10) |
| Galactitol + NaHCO3 (or CO2) | Lactic acid + Formic acid | Hydrogenation of Galactose | −43.56 (−40.86) |
| Xylitol + NaHCO3 (or CO2) | Lactic acid + Formic acid | Hydrogenation of xylose | −33.10 (−30.40) |
| Glycerol + NaHCO3 (or CO2) | Lactic acid + Formic acid | Hydrolysis of triglyceride | −19.48 (16.77) |
| Ethylene glycol + NaHCO3 (or CO2) | Glycolic acid, Lactic acid + Formic acid | Cellulosic biomass cascade reaction | 4.35 (7.05) |
| 1,4- butane-diol + NaHCO3 (or CO2) | γ-butyrolactone + Formic acid | Glucose fermentation/ Succinic acid hydrogenation | −3.68 (−0.97) |
| 2,3- butane-diol + NaHCO3 (or CO2) | Acetoin, Diacetyl + Formic acid | Cellulosic biomass fermentation | 21.64 (24.35) |
| 1,2-pentane-diol + NaHCO3 (or CO2) | Tetrahydrofurfuryl alcohol + Formic acid | Furfural cascade reaction | 17.98 (20.69) |
| 1,5-pentane-diol + NaHCO3 (or CO2) | delta-valerolactone + Formic acid | Furfural cascade reaction | 29.74 (32.45) |
| 1,4-pentane-diol + NaHCO3 (or CO2) | γ-Valerolactone + Formic acid | Hydrogenation of γ-Valerolactone (GVL) | −0.06 (2.64) |
| 1,6-hexane-diol + NaHCO3 (or CO2) | ε-caprolactone + Formic acid | Hydroxymethyl-furfural (HMF) cascade reaction | 31.02 (33.72) |

In addition, the present disclosure, in the presence of the catalyst complex for carbon dioxide conversion reaction, provides a method of producing formic acid from the reaction of at least one among carbon dioxide and inorganic carbonate with hydrocarbon containing at least one hydroxyl group.

The reaction temperature of the method of producing formic acid is preferably room temperature to 240° C., and it is preferable to react at a pressure of 0 bar to 60 bar for within 72 hours. Above 240° C., the reaction rate is quite fast, and by-products may thus be formed.

In addition, the present disclosure, in the presence of the catalyst complex for carbon dioxide conversion reaction, provides a method of preparing a compound through dehydrogenation in a hydroxyl group from the hydrocarbon containing at least one hydroxyl group through reaction of at least one among carbon dioxide and/or inorganic carbonate with hydrocarbon containing at least one hydroxyl group.

In the method of producing a compound through dehydrogenation in the hydroxyl group from the formic acid and/or the hydrocarbon containing at least one hydroxyl group, the amount of the use of the catalyst complex for carbon dioxide conversion reaction is preferably 0.01 wt % to 10 wt % with respect to the hydrocarbon containing at least one hydroxyl group. When the amount of the catalyst is less than 0.01 wt %, catalytic activity may not be sufficient, and when the amount of the catalyst is greater than 10 wt %, it is not economically beneficial in terms of an increase in the catalytic activity according to the amount of the catalyst.

Even when the catalyst complex according to the present disclosure is reused for the carbon dioxide conversion reaction, the catalyst exhibits activity and may thus be effectively used as a heterogeneous catalyst. That is, the catalyst of the present disclosure may exhibit excellent catalytic activity even after being used three or more times.

When a carbon dioxide-derived metal carbonate and hydrocarbon containing at least one hydroxyl group are subjected to reaction using the catalyst, the product is not present as an organic acid, but present in the form of an organic acid salt.

Thereafter, in order to obtain an organic acid as a final product, a desired organic acid has to be separated from unreacted substances or by-products but the separation may not be achieved through conventional distillation processes due to the fact that these organic acids are present in the form of organic acid salts.

Therefore, in order to readily separate the desired product after the reaction, a process of separating the organic acid salt through distillation after reacting with alcohol, etc. for esterification may be performed, and in this case, the yield of the esterification process is not high, thereby causing a decrease in overall process efficiency, and thus, the present disclosure provides a method of overcoming the limitation.

In particular, the present disclosure provides a method of increasing the yield of the esterification process when the inorganic carbonate is metal carbonate and the hydrocarbon containing at least one hydroxyl group is glycerol, thereby increasing the efficiency of the overall carbon dioxide conversion process.

The present disclosure provides, as a solution, an esterification method capable of obtaining an ester product with high yield through an esterification reaction of an organic acid metal salt such as metal lactate and metal formate with $C_4$ to $C_8$ alcohols without miscibility with water, and through the process, the separation efficiency increases, thereby ultimately achieving an increase in yield of target products of the carbon dioxide conversion process.

To be specific, the process of carbon dioxide conversion to increase the esterification yield according to the present disclosure may include a) in the presence of a catalyst complex for carbon dioxide conversion reaction, performing a simultaneous conversion reaction of a carbon dioxide-derived metal carbonate and glycerol to obtain a reaction product, b) forming a mixture in which at least one selected from among $C_4$ to $C_8$ alcohols and trialkyl phosphate (TAP) are added to the obtained reaction product, c) removing some moisture from the mixed solution, and d) performing carbonation and esterification by adding carbon dioxide ($CO_2$) to the mixed solution having some moisture above removed therefrom, and performing an esterification reaction of the mixture to synthesize alkyl lactate and alkyl formate.

After step d), the method further includes e) separating the alkyl lactate and the alkyl formate produced in step d) from each other through conventional methods such as distillation, and f) recovering the metal carbonate produced as a reaction by-product in step d), and recycling the metal carbonate to the simultaneous conversion reaction of glycerol and metal carbonate.

In addition, the present disclosure further includes g) hydrolyzing the alkyl lactate and the alkyl formate to produce a lactic acid and a formic acid after the separation process described above when a desired product is an organic acid such as lactic acid and formic acid.

In step a), the simultaneous conversion reaction of metal carbonate and glycerol is one of the mobile hydrogenation reactions generated when hydrogen of glycerol is transferred to carbonate anions of metal carbonate, and the catalyst complex uses the catalyst according to the present disclosure to perform the reaction. The lactate and formate obtained as reaction products react with metal cations of the metal carbonate present in the reaction solvent to be in the form of a metal salt.

The metal carbonate may be a carbon dioxide-derived metal carbonate produced when carbon dioxide combines with a metal, etc., and preferably may be a metal carbonate or metal hydrogen carbonate compound. The metal carbonate produced by combining with the metal ions may be, for example, at least one selected from among $MgCO_3$, $CaCO_3$, $KHCO_3$, $K2CO_3$, $NaHCO_3$, $Na_2CO_3$, $LiHCO_3$, $Li_2CO_3$, $FeCO_3$, $CuCO_3$, $Ag_2CO_3$, $BaCO_3$, $SrCO_3$, $MnCO_3$, $Mn(CO_3)_2$, $RbHCO_3$, $Rb_2CO_3$, $CsHCO_3$, and $Cs_2CO_3$, preferably at least one selected from among $KHCO_3$, $K_2CO_3$, $NaHCO_3$, and $Na_2CO_3$.

The simultaneous conversion reaction of a carbon dioxide-derived metal carbonate and glycerol in step a) is performed in a solution containing water, and in the aqueous solution after the reaction, metal formate and metal lactate are present together as reaction products.

Thereafter, in step b), at least one alcohol selected from among $C_4$ to $C_8$ alcohols and trialkyl phosphate (TAP) are added to the aqueous solution of the organic acid metal salt containing metal lactate and metal formate to produce a mixed solution. The molar ratio of the metal lactate/metal formate may be 0.05 to 20, and preferably 0.01 to 10.

It is preferable that alcohol in step b) has 4 to 8 carbon atoms, and when the number of carbon atoms is less than 4, alcohol forms a single phase with the aqueous solution, causing difficulty separating moisture, and the partial pressure of the low-boiling alcohol is too high at the reaction temperature, causing difficulty injecting carbon dioxide which is used as a reactant in the carbonation process of the subsequent stage, and when the number of carbon atoms is greater than 8, the yield of the esterification reaction decrease. As alcohol, butanol having 4 carbon atoms is preferred, and n-butanol is most preferred.

The trialkyl phosphate (TAP) has a quite high boiling point of 190° C. or higher to hardly evaporate even in a moisture removal process and the esterification process, and is stably present. The trialkyl phosphate may contain a C1 to C20 alkyl group, preferably, a C3 to C14 alkyl group, most preferably, an alkyl group having the same number of carbon atoms as the added alcohol to benefit uniform reaction and purity control of final products.

The number of moles of alcohol added in step b) is preferably 1 to 50 as a ratio to the sum of the number of moles of metal lactate and formate, and when the addition ratio of alcohol is less than 1, the yield for derivatives may be limited. In addition, when the addition ratio of the alcohol is greater than 50, it is not economically beneficial due to the excess use of alcohol, and excess energy consumption may be caused during the recovery process.

In this case, it is preferable that the molar ratio of alcohol to trialkyl phosphate added in step b) is 1:5 to 5:1, and when trialkyl phosphate is added in an excess amount, it is not economically beneficial due to the fact that excess energy is consumed in the purification process for recovering the trialkyl phosphate. The trialkyl phosphate may be added in step b), but may be added in step d) below after removing moisture, instead of step b). Even when trialkyl phosphate is added in step d), the molar ratio of alcohol added in step b) and the molar ratio of trialkyl phosphate are equally applied.

Subsequently, step c) refers to removing some moisture from the mixture of step b). The method of removing the moisture may use conventional methods such as membrane separation, absorption, extraction, and distillation, and preferably, a method of exclusively discharging moisture to the outside without loss of the reactant and alcohol through a series of processes such as distillation, external condensation, and reflux of an organic phase due to liquid-liquid phase separation during or after the reaction may be used. Such removing of moisture may be performed independently at atmospheric pressure outside the reaction system, but may not be beneficial in terms of energy management.

The removing of moisture at atmospheric pressure is preferably performed at a temperature of 100° C. to 120° C. When the moisture is removed at a temperature of less than 100° C., the removal rate of moisture is slow as a downside, and when the moisture is removed at a temperature of greater than 120° C., an organic acid polymer may be partially formed as a downside. Further, the removing of moisture may be performed by adding alkyl phosphate, but is not limited thereto.

The amount of moisture remaining after the removing of moisture in step c) may be 1 wt % to 20 wt %. In order to maintain the amount of moisture below 1 wt %, the moisture removal process has to be performed for long, and when the amount of moisture is greater than 20 wt %, the esterification reaction rate may be significantly reduced, and the yields of ultimately obtained lactic acid and formic acid derivatives may significantly decrease.

Step d) refers to a carbonation and esterification process in which carbon dioxide ($CO_2$) is added to the mixture having moisture removed therefrom after step c), and the esterification process is performed to synthesize an ester product of organic acid and alcohol.

As described above, the trialkyl phosphate may be added in step d) instead of step b).

The carbonation is to replace the metal ions of the organic acid metal salt with hydrogen, and carbon dioxide is added to the mixture after step c) to combine with the metal ions so as to form metal carbonate. In this case, carbon dioxide gas may be supplied while being pressurized in a range of atmospheric pressure to 60 bar.

The esterification refers to a process of performing an ester reaction of the lactate, formate, and alcohol to produce alkyl lactate and alkyl formate. In this case, the reaction temperatures of the carbonation and esterification processes are preferably 120° C. to 200° C. In general, in the esterification reaction, an acid catalyst such as sulfuric acid is added to increase the yield of the esterification reaction. However, in the present disclosure, the yield of the esterification reaction may stay high without using the acid catalyst.

When the carbonation reaction is performed, lactic acid or formic acid is produced, and due to their hydrophilic properties, they are distributed in a higher concentration in an aqueous phase than in an organic phase, and when exposed to high temperatures, the side reaction rate in which oligomers are formed may significantly increase compared to the esterification reaction. When trialkyl phosphate is added, the resulting initial lactic acid is uniformly dispersed in an overall reaction medium, and the resulting alkyl derivatives of lactic acid and formic acid serve as amphoteric materials to promote mass transfer at a phase interface, thereby evenly keeping the acidity of the reaction medium in the acidic levels and greatly suppressing side reactions of the esterification reaction, and thus, despite using alcohols having 4 or more carbon atoms, the resulting esterified product has a fairly dramatic yield improvement of approaching 90%, and as shown in an example of the present disclosure, when the simultaneous conversion reactant having formate added thereto is applied as a raw material, a nearly 90% to 100% of highly ideal esterified product may be produced.

Step e) refers to a process of separating the alkyl lactate and the alkyl formate produced in step d). The separation may be readily performed using a distillation method.

Metal lactate and metal formate produced as reaction products of the simultaneous conversion reaction of metal carbonate and glycerol do not easily separate through conventional methods such as distillation due to the presence of a metal salt, but through the esterification reaction in the present disclosure, the alkyl lactate and the alkyl formate are converted into a form suitable for distillation, thereby allowing separation from the reaction products of the simultaneous conversion reaction to be well performed.

Step f) of the present disclosure refers to a process of recycling the metal carbonate precipitated in the carbonation and esterification processes to a simultaneous conversion reaction of glycerol and metal carbonate. In the carbonation and esterification processes, the metal cation combined to metal lactate and metal formate reacts with carbonate ions derived from carbon dioxide to produce metal carbonate, and the resulting metal carbonate has low solubility in solvents such as alcohol to be precipitated as crystals. The precipitated crystals are recovered through filtration, etc. and returns to the simultaneous conversion reaction with glycerol for reuse, and thus, resources may be efficiently used.

Step g) refers to a process of performing hydrolysis by adding water to the separated alkyl lactate and alkyl formate.

In the hydrolysis reaction, it is preferable to add an excess of 2 to 100 times the number of moles of water to the number of moles of alkyl lactate and alkyl formate, and it is preferable that the reaction temperature of the hydrolysis process is 30° C. to 120° C. in the presence of an inorganic acid or an ion exchange resin acid catalyst.

In addition, as an embodiment of the present disclosure, the organic solvent and alcohol separated in step d) and the alcohol produced in step g) are separated, and an organic solvent recovery and a resupply process in which the resultant is recycled to step b) is additionally included to reuse the organic solvent, thereby using resources efficiently.

In addition, in the present disclosure, as an inorganic salt precursor of the metal carbonate, an alkali salt produced in another chemical process may be used.

Figure 1:
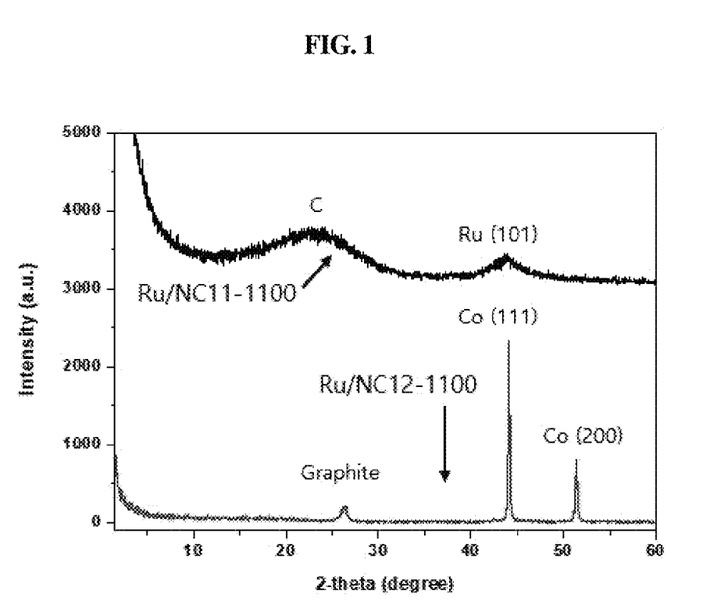
FIG. 1 is an X-ray diffraction (XRD) graph according to an embodiment of the present disclosure.
Figure 2:
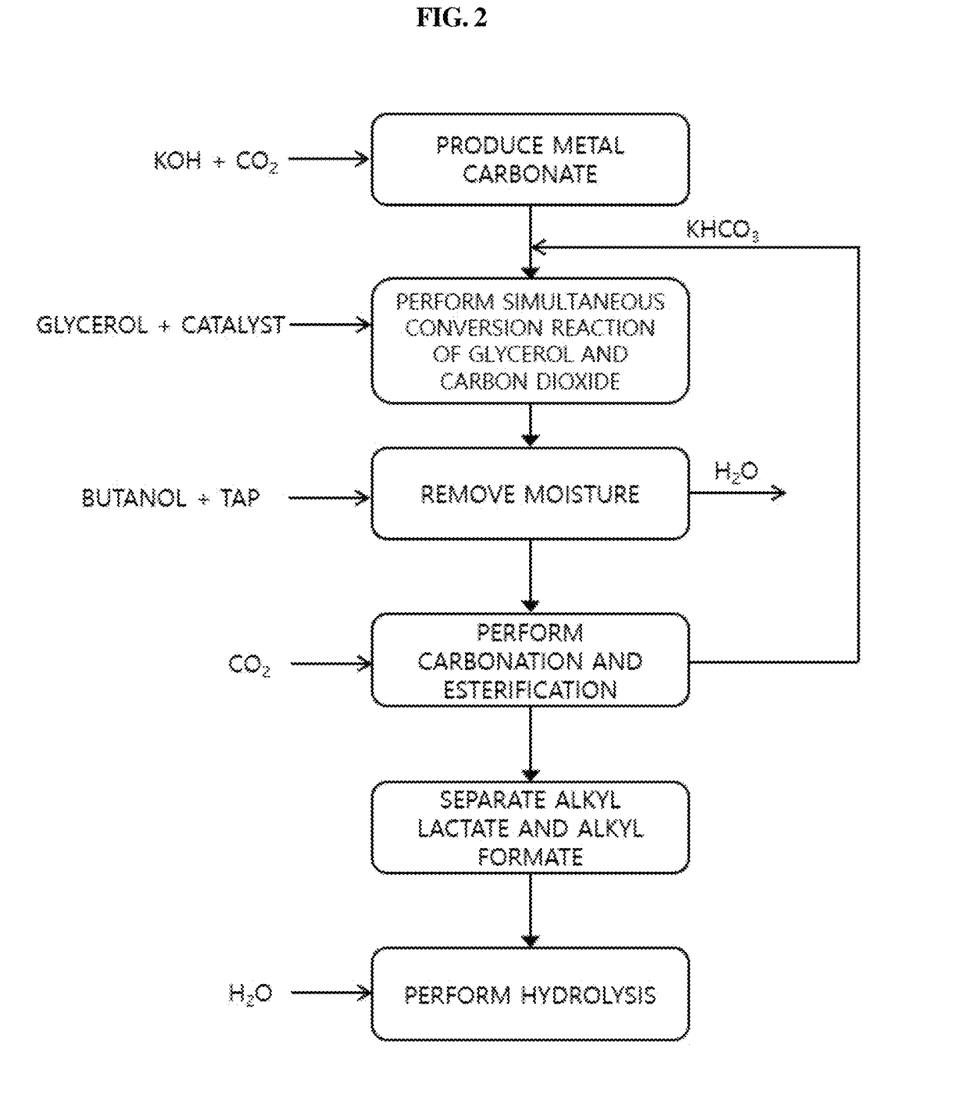
FIG. 2 is a process block diagram illustrating a process according to an embodiment of the present disclosure.

FIG. 2 shows a schematic process diagram illustrating carbon dioxide simultaneous conversion starting from an alkali salt produced in another chemical process, and then production of lactic acid and formic acid as an embodiment of the present disclosure.

According to FIG. 2, a carbon dioxide conversion reaction system of the present disclosure includes A) generating metal carbonate from the reaction of metal compounds and carbon dioxide ($CO_2$), B) synthesizing metal lactate and metal formate from the simultaneous conversion reaction of metal carbonate and glycerol, C) adding at least one alcohol selected from among $C_4$ to $C_8$ alcohols and an inert organic solvent to an aqueous solution containing metal lactate and metal formate obtained in the simultaneous conversion reaction, and discharging and removing a predetermined portion of water to the outside of the process through continuous distillation and extraction, D) performing carbonation and esterification in which carbon dioxide ($CO_2$) is added to the organic solvent containing metal lactate and metal formate to synthesize alkyl lactate and alkyl formate, and E) separating alkyl lactate and alkyl formate obtained in step D).

After step E), the system may further include F) hydrolyzing the obtained alkyl lactate and alkyl formate to produce a lactic acid and a formic acid.

In step A), the metal carbonate is produced by reacting a metal compound with carbon dioxide, and the metal compound may be, for example, KOH obtained as a by-product in a chloro-alkali process, and carbon dioxide in contact with KOH may be used by capturing $CO_2$ contained in fuel combustion exhaust gas of power plants and steelworks, or $CO_2$ generated from natural gas reforming for hydrogen production. The metal carbonate produced therefrom is potassium carbonate ($K_2CO_3$) and/or potassium hydrogen carbonate ($KHCO_3$).

Thereafter, in step B), carbon dioxide conversion reaction for synthesizing potassium lactate and potassium formate from the simultaneous conversion reaction of the metal carbonate (potassium carbonate and/or potassium hydrogen carbonate) prepared above and glycerol on the catalyst complex is performed.

The simultaneous conversion reaction process of step B) is a simultaneous conversion reaction of metal carbonate (potassium carbonate and/or potassium hydrogen carbonate) and glycerol, and is performed through a mobile hydrogenation process in which hydrogen from glycerol is transferred to an anion of potassium carbonate.

As the glycerol, waste glycerol generated as a by-product in biodiesel production may be used. Biodiesel is a means of solving environmental and energy issues, and in recent years, the amount of use of biodiesel is on the rise, and in the biodiesel production, glycerol which is about 10% of raw material fat or oil is produced as a by-product. However, the utilization of the glycerol is not well positioned, and with an increase in biodiesel production, glycerol produced as a by-product is supplied in an excess amount and thus, the utilization of glycerol is in trouble. In the present disclosure, glycerol is converted to lactic acid which is highly utilized to resolve both issues of excess glycerol and carbon dioxide removal together.

In step B), the simultaneous conversion reaction of metal carbonate (potassium carbonate and/or potassium hydrogen carbonate) and glycerol may be accelerated using a catalyst.

The catalyst may include at least one among a catalyst complex in which a noble metal is supported as an active metal on a support including a graphite carbon body, a catalyst encapsulating organic metals in MOF, and a complex metal catalyst in which, as an active metal, one of noble metals and at least one selected from among other transition metals are supported on a support.

The simultaneous conversion reaction temperature of step B) is preferably room temperature to 240° C., and it is preferable to react within 72 hours at a pressure of 0 bar to 60 bar.

Next, in step C), an organic solvent and at least one alcohol selected from among $C_4$ to $C_8$ alcohols are added to the reaction product in which potassium lactate and potassium formate obtained in the simultaneous conversion reaction process remain, and the mixture is subjected to continuous distillation and extraction to remove moisture.

The molar ratio of at least one alcohol selected from among $C_4$ to $C_8$ alcohols added in step C) to trialkyl phosphate (TAP) as an inert organic solvent is preferably 1:5 to 5:1, and the vapor mixture (alcohol and water) discharged to the outside of the reactor through distillation forms a heterogeneous liquid phase having two phases of an organic solvent layer and an aqueous solution layer condensed through cooling, the alcohol returns to the reactor through liquid-liquid phase separation, and the aqueous phase may be discharged out of the system. At least one alcohol selected from among $C_4$ to $C_8$ above is preferably butanol. In step C), trialkyl phosphate, which is an inert organic solvent, may be added together with alcohol, but may be added after alcohol is added first and moisture is removed.

Subsequently, in step D), carbon dioxide ($CO_2$) is added to an organic solvent containing potassium lactate and potassium formate to produce a lactic acid and a formic acid, carbonation and esterification processes to synthesize alkyl lactate and alkyl formate from the esterification process of lactic acid and formic acid are continuously performed, and as a by-product, potassium ions and carbonate ions combine to form metal carbonate (potassium carbonate and/or potassium hydrogen carbonate) again. The supply pressure of carbon dioxide, and the reaction temperature and reaction time of the esterification process are the same as described above.

In addition, in step D), the generated metal carbonate is precipitated, and the precipitated metal carbonate may be recycled to step B), which is a process of simultaneous conversion of glycerol and carbon dioxide for reuse.

Subsequently, in step E), a separation process for separating alkyl lactate and alkyl formate obtained in step D) is performed. The separation may be performed using a known distillation method, etc.

In step F), water ($H_2O$) is added to the separated alkyl lactate and alkyl formate to perform a hydrolysis reaction so as to produce a lactic acid and a formic acid.

In the hydrolysis reaction, it is preferable to add an excess of 2 to 100 times the number of moles of water to the number of moles of alkyl lactate and alkyl formate, and the reaction temperature of the hydrolysis process is preferably 30° C. to 120° C. in the presence of an inorganic acid or an ion exchange resin acid catalyst.

In addition, as an example, alcohol and trialkyl phosphate separated in steps E) and F) may be recycled to step C), thereby efficiently using resources.

Hereinafter, the present disclosure will be described in more detail through specific examples. The following examples are presented only to aid understanding of the present disclosure, and the scope of the present disclosure is not limited thereto.

Preparation Example 1: Ru(1)/NC-900 Catalyst

Preparation Example 1-1. Preparation of Ru(1)/ZIF-8

Ru(1)/ZIF-8 in which Ru(acac)$_3$ (ruthenium acetylacetonate) was encapsulated in the pores of ZIF-8 was prepared using an in-situ method.

64 mmol of Zn(NO$_3$)$_2$.6H$_2$O and 4 mmol of Ru(acac)$_3$ were dissolved in 480 mL of methanol while being stirred for an hour. 256 mmol of 2-methylimidazole was dissolved in a solution in which 96 mL of DMF and 64 mL of methanol were mixed. The two solutions were sequentially poured into a teflon-lined autoclave, and a reactor was placed in an oven and heated to 120° C. for 4 hours. After cooling the reactor with cold water, the obtained solution was centrifuged at 7000 rpm for 10 minutes and washed three times with methanol to obtain powder, and then the obtained powder was dried in a vacuum oven at 100° C. for 12 hours to prepare Ru(1)/ZIF-8 in which Ru(acac)$_3$ was encapsulated in the pores of ZIF-8.

Preparation Example 1-2. Preparation of Ru(1)/NC-900

Ru(1)/NC-900 in which a Ru metal was highly dispersed in a graphite support was prepared as follows.

The Ru(1)/ZIF-8 prepared in Preparation Example 1-1 was placed in a boat-type alumina crucible, and the crucible was placed in a tube-type furnace. The furnace was subjected to injection of 5% H$_2$/Ar gas, at a temperature raised from room temperature to 800° C. at a rate of 5° C./min, was carbonized at 900° C. for 3 hours, and was cooled to room temperature to prepare Ru(1)/NC-900.

The Zn evaporated during the firing process, and only Ru was actually present as an active metal. In the finally prepared catalyst, the amount of Ru is 1.5 wt %.

Preparation Example 2: Ru(1)Co/NC-900 Catalyst

Preparation Example 2-1. Preparation of Ru(1)/ZnCo—ZIF

Ru(1)/ZnCo—ZIF in which Ru(acac)$_3$ (ruthenium acetylacetonate) was encapsulated in the pores of ZnCo—ZIF was prepared using an in-situ method.

64 mmol of Zn(NO$_3$)$_2$.6H$_2$O, 64 mmol of Co (NO$_3$)$_2$.6H$_2$O, and 4 mmol of Ru(acac)$_3$ were dissolved in 480 mL of methanol while being stirred for an hour. 256 mmol of 2-methylimidazole was dissolved in a solution in which 96 mL of DMF and 64 mL of methanol were mixed. The two solutions were sequentially poured into a teflon-lined autoclave, and a reactor was placed in an oven and heated to 120° C. for 4 hours. After cooling the reactor with cold water, the obtained solution was centrifuged at 7000 rpm for 10 minutes and washed three times with methanol, and then the obtained powder was dried in a vacuum oven at 100° C. for 12 hours to prepare Ru(1)/ZnCo—ZIF in which Ru(acac)$_3$ was encapsulated in the pores of ZnCo—ZIF.

Preparation Example 2-2. Preparation of Ru(1)Co/NC-900

Ru(1)Co/NC-900 in which a Ru metal was highly dispersed in a graphite support and Co nanoparticles were present was prepared as follows.

The Ru(1)/ZnCo—ZIF prepared in Preparation Example 2-1 was placed in a boat-type alumina crucible, and the crucible was placed in a tube-type furnace. The furnace was subjected to injection of 5% H$_2$/Ar gas, at a temperature raised from room temperature to 800° C. at a rate of 5° C./min, was carbonized at 900° C. for 3 hours, and was cooled to room temperature to prepare Ru(1)Co/NC-900 in which Ru metal was highly dispersed in the graphite support and Co nanoparticles were present. The Zn evaporated during the firing process, and only Ru and Co were actually present as an active metal, and the amount of Ru is 1 wt %, and the amount of Co is 47 wt %.

Preparation Example 3: Ru(3)/NC-900 Catalyst

Preparation Example 3-1. Preparation of Ru(3)/ZIF-8

Ru(3)/ZIF-8 in which Ru$_3$(CO)$_{12}$ (triruthenium dodecacarbonyl) was encapsulated in the pores of ZIF-8 was prepared using an in-situ method.

64 mmol of $Zn(NO_3)_2 \cdot 6H_2O$ and 2.4 mmol of $Ru_3(CO)_{12}$ were dissolved in 480 mL of methanol while being stirred for an hour. 256 mmol of 2-methylimidazole was dissolved in a solution in which 96 mL of DMF and 64 mL of methanol were mixed. The two solutions were sequentially poured into a teflon-lined autoclave, and a reactor was placed in an oven and heated to 120° C. for 4 hours. After cooling the reactor with cold water, the obtained solution was centrifuged at 7000 rpm for 10 minutes and washed three times with methanol, and then the obtained powder was dried in a vacuum oven at 100° C. for 12 hours to prepare Ru(3)/ZIF-8 in which $Ru(acac)_3$ was encapsulated in the pores of ZIF-8.

Preparation Example 3-2. Preparation of Ru(3)/NC-900

Ru(3)/NC-900 in which a Ru metal was highly dispersed in a graphite support was prepared as follows.

The Ru(3)/ZIF-8 prepared in Preparation Example 3-1 was placed in a boat-type alumina crucible, and the crucible was placed in a tube-type furnace. The furnace was subjected to injection of 5% $H_2$/Ar gas, at a temperature raised from room temperature to 900° C. at a rate of 5° C./min, was carbonized at 900° C. for 3 hours, and was cooled to room temperature to prepare Ru(3)/NC-900 in which a Ru metal was highly dispersed in the graphite support. The Zn evaporated during the firing process, and only Ru was actually present as an active metal. In the finally prepared catalyst, the amount of Ru is 1.5 wt %.

Preparation Example 4: Ru(3)Co/NC-900 Catalyst

Preparation Example 4-1. Preparation of Ru(3)/ZnCo—ZIF

Ru(3)/ZnCo—ZIF-8 in which $Ru_3(CO)_{12}$ (ruthenium acetylacetonate) was encapsulated in the pores of ZnCo—ZIF-8 was prepared using an in-situ method.

64 mmol of $Zn(NO_3)_2 \cdot 6H_2O$, 64 mmol of $Co(NO_3)_2 \cdot 6H_2O$, and 2.4 mmol of $Ru(acac)_3$ were dissolved in 480 mL of methanol while being stirred for an hour. 256 mmol of 2-methylimidazole was dissolved in a solution in which 96 mL of DMF and 64 mL of methanol were mixed. The two solutions were sequentially poured into a teflon-lined autoclave, and a reactor was placed in an oven and heated to 120° C. for 4 hours. After cooling the reactor with cold water, the obtained solution was centrifuged at 7000 rpm for 10 minutes and washed three times with methanol to obtain powder, and then the obtained powder was dried in a vacuum oven at 100° C. for 12 hours to prepare Ru(3)/ZnCo—ZIF in which $Ru_3(CO)_{12}$ (ruthenium acetylacetonate) was encapsulated in the pores of ZnCo—ZIF.

Preparation Example 4-2. Preparation of Ru(3)Co/NC-900

Ru(3)/Co/NC-900 in which a Ru metal was highly dispersed in a graphite support and Co nanoparticles were present was prepared as follows.

The Ru(3)/ZnCo—ZIF prepared in Preparation Example 4-1 was placed in a boat-type alumina crucible, and the crucible was placed in a tube-type furnace. The furnace was subjected to injection of 5% $H_2$/Ar gas, at a temperature raised from room temperature to 900° C. at a rate of 5° C./min, was carbonized at 900° C. for 3 hours, and was cooled to room temperature to prepare Ru(3)/Co/NC-900 in which a Ru metal was highly dispersed in the graphite support and Co nanoparticles were present. The Zn evaporated during the firing process, and only Ru and Co were actually present as an active metal. In the finally prepared catalyst, the amount of Ru is 2.7 wt %, and the amount of Co is 11.2 wt %.

Preparation Example 5: Ru(3)/NC11-1100 Catalyst

Preparation Example 5-1. Preparation of Ru(3)/ZIF-11

Ru(3)/ZIF-11 in which Ru(3) cluster ($[Ru_3O(OAc)_6(H_2O)_3]OAc$) was encapsulated in the pores of ZIF-11 was prepared using an in-situ method as follows.

10 mmol of benzimidazole was dissolved in 48 g of methanol, and then 46 g of toluene and 1.3 ml of $NH_4OH$ aqueous solution were added thereto. Thereafter, 0.1 mmol of Ru(3) cluster ($[Ru_3O(OAc)_6(H_2O)_3]OAc$) was added to the solution, and then 5 mmol of $Zn(acet)_2 \cdot 2H_2O$ was added thereto. The solution was stirred for 4 hours, centrifuged at 7000 rpm for 10 minutes, and washed three times with methanol to obtain powder, and then the obtained powder was dried for 12 hours in a vacuum oven at 100° C. to prepare Ru(3)/ZIF-11 in which Ru(3) cluster ($[Ru_3O(OAc)_6(H_2O)_3]OAc$) was encapsulated in the pores of ZIF-11.

Preparation Example 5-2. Preparation of Ru(3)/NC11-1100

Ru(3)/NC11-1100 in which a Ru metal was highly dispersed in a graphite support was prepared as follows.

Ru(3)/ZIF-11 prepared in Preparation Example 5-1 was placed in a boat-type alumina crucible, and the crucible was placed in a tube-type furnace. The furnace was subjected to injection of 5% $H_2$/Ar gas, at a temperature raised from room temperature to 1100° C. at a rate of 5° C./min, was carbonized at 1100° C. for 3 hours, and was cooled to room temperature to prepare Ru(3)/NC11-1100 in which a Ru metal was highly dispersed in the graphite support. The Zn evaporated during the firing process, and only Ru was actually present as an active metal. In the finally prepared catalyst, the amount of Ru is 0.9 wt %.

Preparation Example 6: Ru(3)Co/NC12-1100 Catalyst

Preparation Example 6-1. Preparation of Ru(3)/Co—ZIF-12

Ru(3)/Co—ZIF-12 in which Ru(3) cluster ($[Ru_3O(OAc)_6(H_2O)_3]OAc$) was encapsulated in the pores of Co—ZIF-12 was prepared using an in-situ method as follows.

10 mmol of benzimidazole was dissolved in 48 g of methanol, and then 46 g of toluene and 1.3 ml of $NH_4OH$ aqueous solution were added thereto. Thereafter, 0.1 mmol of Ru(3) cluster was added to the solution and then 5 mmol of $Co(acet)_2 \cdot 4H_2O$ was added thereto. The solution was stirred for 4 hours, centrifuged at 7000 rpm for 10 minutes, and washed three times with methanol to obtain powder, and then the obtained powder was dried for 12 hours in a vacuum oven at 100° C. to prepare Ru(3)/Co—ZIF-12 in which Ru(3) cluster ($[Ru_3O(OAc)_6(H_2O)_3]OAc$) was encapsulated in the pores of Co—ZIF-12.

Preparation Example 6-2. Preparation of Ru(3)Co/NC12-1100

Ru(3)Co/NC12-1100 in which a Ru metal was highly dispersed in a graphite support and Co nanoparticles were present was prepared as follows.

The Ru(3)/Co—ZIF-12 prepared in Preparation Example 6-1 was placed in a boat-type alumina crucible, and the crucible was placed in a tube-type furnace. The furnace was subjected to injection of 5% $H_2$/Ar gas, at a temperature raised from room temperature to 1100° C. at a rate of 5° C./min, was carbonized at 1100° C. for 3 hours, and was cooled to room temperature to prepare Ru(3)Co/NC12-1100 in which a Ru metal was highly dispersed in the graphite support and Co nanoparticles were present.

Ru and Co were present as an active metal. In the finally prepared catalyst, the amount of Ru is 2.36 wt %, and the amount of Co is 47 wt %.

Examples 1 to 3 and Comparative Examples 1 to 3 glycerol and $K_2CO_3$ were added to 35.38 g of distilled water, and optionally KOH was added to a high-pressure reactor to have the concentration shown in Tables 2 and 3 below, and then 0.2 g of catalyst prepared in Preparation Example was added, and nitrogen was filled thereto to adjust the pressure to 26 bar. The reactor was raised to the reaction temperature, and the reaction was performed at 180° C. or 220° C. for 12 hours. After cooling the reactor to room temperature, the solution obtained by filtering the catalyst was quantitatively analyzed through HPLC, and the obtained powder was washed with methanol and dried.

The results of the simultaneous conversion reaction are shown in Tables 2 and 3 below.

TABLE 2

| No | Cat | Temp (° C.) | Glycerol (M) | $K_2CO_3$ (M) | LA Yield (%) | FA Yield (%) |
|---|---|---|---|---|---|---|
| Comparative Example 1 | Ru(1)/NC-900 | 180 | 4 | 1 | 14.3 | 13.3 |
| Comparative Example 2 | Ru(3)/NC-900 | 180 | 4 | 1 | 16.5 | 11.0 |
| Example 1 | Ru(1)Co/NC-900 | 180 | 4 | 1 | 14.2 | 22.8 |
| Example 2 | Ru(3)Co/NC-900 | 180 | 4 | 1 | 16.2 | 25.1 |

TABLE 3

| No | Cat | Temp (° C.) | Glycerol (M) | $K_2CO_3$ (M) | KOH (M) | LA/FA Yield (%) | LA sel (%) | 1,2-PDO |
|---|---|---|---|---|---|---|---|---|
| Comparative Example 3 | Ru(3)/NC11-1100 | 220 | 4 | 2 | 2 | 47.3/25.1 | 59.3 | 13.6 |
| Example 3 | Ru(3)Co/NC12-1100 | 220 | 4 | 2 | 2 | 55.5/41.4 | 57.3 | 5.8 |

In Examples 1 and 2, precursors of the active metal are different in the same metal. The different precursors cause a slight difference in the activity but generally a similar level of activity is shown.

Comparative Examples 1 and 2 above each used the same active metal precursors as those in Examples 1 and 2, but a single Ru metal without having Co was used. When more Co was added to Ru, similar results are shown compared with the results of lactic acid, but it was found that the formic acid yield increased from 13.3% to 22.8% and from 11.0% to 25.1%.

Example 3 and Comparative Example 3 show experimental results at 220° C. Compared to the experimental results at 180° C., lactic acid (LA) and formic acid (FA) both show an increase in yield, but the yield of lactic acid increased greater than the yield of formic acid.

Compared to the experimental results at 220° C., it was found that when using Ru and Co complex metals as an active metal, the yields of lactic acid and formic acid increased, but particularly, the yield of FA significantly increased.

From the above results, it is found that when a transition metal, which is a non-noble metal, is included with a noble metal, the yield of formic acid increases.

Therefore, when the catalyst according to the present disclosure is used, formic acid may be produced in a higher yield in the carbon dioxide conversion through a reaction of at least one among carbon dioxide and/or inorganic carbonate with hydrocarbon containing at least one hydroxyl group.

Examples 4 to 13 and Comparative Examples 4 to 7

Examples 4 to 13 and Comparative Examples 4 to 7 show experimental results of the effect of an increase in the yield of the esterification reaction of potassium lactate and potassium formate produced through the reaction of glycerol and potassium carbonate according to the present disclosure.

Using a Dean-Stark trap, moisture was removed from potassium lactate and potassium formate obtained from the simultaneous conversion reaction of glycerol, and the mixture was used as a raw material. A high-concentration potassium lactate salt was prepared by using a potassium lactate salt solution containing a large amount of water through a moisture removal process below. The high-concentration potassium lactate salt was used to prepare a simulated composition containing potassium lactate salt or to prepare a reactant having a constant amount.

850 g of a 60 wt % potassium lactate salt (Aldrich, catal. #60389) solution was added to a flask, and the water bath temperature and the cooling temperature were maintained at about 50° C. and at about 2° C., respectively. Thereafter, a vacuum pump was connected thereto to control the final vacuum level in the reactor to be kept to 15 mbar, and then, the reactant was subjected to concentration for 2 hours. The concentration of the concentrated reactant was determined through cation chromatography (YS-50 4D-P column, Futecs) analysis, and the concentration of potassium lactate salt prepared through moisture removal was 88.5 wt %.

Tributyl phosphate, butanol, dodecane, etc. were added to the concentrated reaction solution to the amount shown in Table 4 below, and then the mixture was placed into a 300 ml high-pressure reactor and sufficiently stirred at 500 rpm for 15 minutes through an impeller connected through a magnetic drive at room temperature. Thereafter, heat was supplied to the reactor containing the reactant, and when the temperature of the final reaction solution reached a target value, carbon dioxide was pressurized at about 50 bar to perform carbonation and esterification reactions for a predetermined period of time so as to obtain butyl lactate and butyl formate. After the reaction was completed, the resultant was analyzed using liquid chromatography (HPLC with Optimapak C18 Column (250 mm, 5 micron), UV detector ($\lambda$=210 nm)), and the values thereof are shown in Table 4.

In the table below, K-LA refers to a mass value in which the concentration of potassium lactate salt is converted into an aqueous solution with 88.5 wt %, K-FA represents a potassium formate salt, BuOH represents butanol, TBP represents tributyl phosphate, Bu-LA represents butyllactate, and Bu-FA represents butyl formate, respectively.

TABLE 4

| Type | Reaction temperature (° C.) | Reaction time (hr) | $CO_2$ Pressure (bar) | $N_2$ Pressure (Bar) | K-LA (g) | K-FA (g) | BuOH (g) | TBP (g) | Dodecane (g) | Yield (%) Bu-LA | Bu-FA |
|---|---|---|---|---|---|---|---|---|---|---|---|
| Comparative Example 4 | 100 | 2 | 50 | — | 12 | 4 | 60 | 53 | — | 1 | 2 |
| Example 4 | 140 | 2 | 50 | — | 12 | 4 | 60 | 53 | — | 26 | 10 |
| Example 5 | 160 | 2 | 50 | — | 12 | 4 | 60 | 53 | — | 83 | 82 |
| Example 6 | 180 | 2 | 50 | — | 12 | 4 | 60 | 53 | — | 92 | 82 |
| Example 7 | 160 | 1 | 50 | — | 12 | 4 | 60 | 53 | — | 64 | 61 |
| Example 8 | 160 | 3 | 50 | — | 12 | 4 | 60 | 53 | — | 90 | 90 |
| Example 9 | 160 | 4 | 50 | — | 12 | 4 | 60 | 53 | — | 89 | 86 |
| Example 10 | 160 | 5 | 50 | — | 12 | 4 | 60 | 53 | — | 85 | 86 |
| Example 11 | 160 | 6 | 50 | — | 12 | 4 | 60 | 53 | — | 87 | 89 |
| Example 12 | 180 | 1 | 50 | — | 12 | 4 | 60 | 53 | — | 94 | 88 |
| Example 13 | 180 | 6 | 50 | — | 12 | 4 | 60 | 53 | — | 99 | 38 |
| Comparative Example 5 | 180 | 6 | 50 | — | 14 | — | 71 | — | — | 9 | — |
| Comparative Example 6 | 180 | 6 | 50 | — | 14 | — | 71 | 53 | — | 89 | — |
| Comparative Example 7 | 180 | 2 | 50 | — | 12 | 4 | 60 | — | 34 | 3 | 13 |

<Changes in Esterification Yield by Reaction Temperature and Reaction Time>

Figure 3:
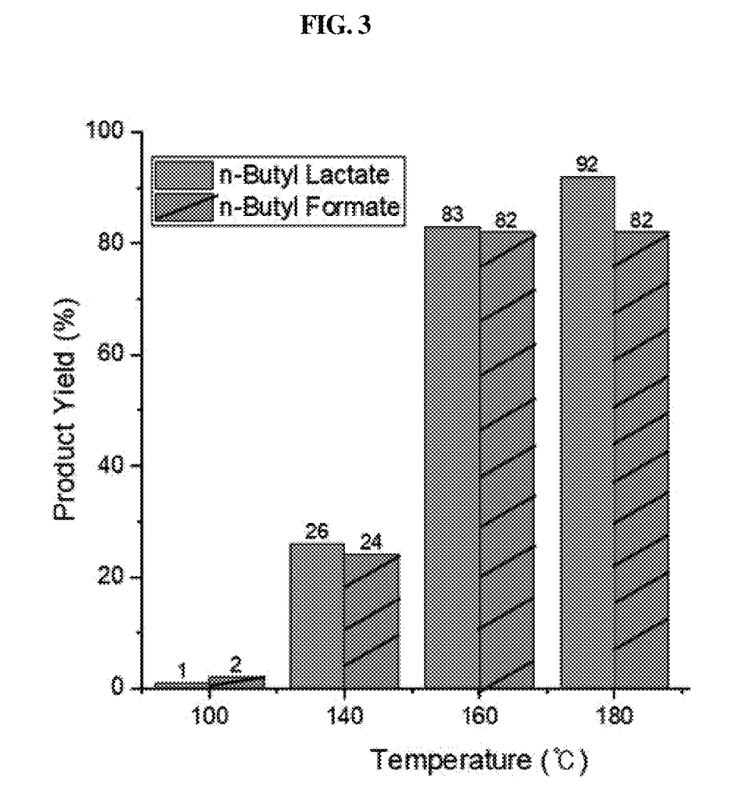
FIG. 3 is a graph showing the yield of butyl lactate and butyl formate with a reaction time of 2 hours at different reaction temperatures.

Examples 4 to 6 and Comparative Example 1 above were experiments performed at different reaction temperatures, and are shown again in FIG. 3. When the reaction temperature is 100° C., the yields of butyl lactate and butyl formate are about 1% and about 2%, respectively, and thus, alkylation reaction was hardly shown, indicating that a certain temperature or higher has to be met to accelerate the esterification reaction according to the present disclosure.

Figure 4:
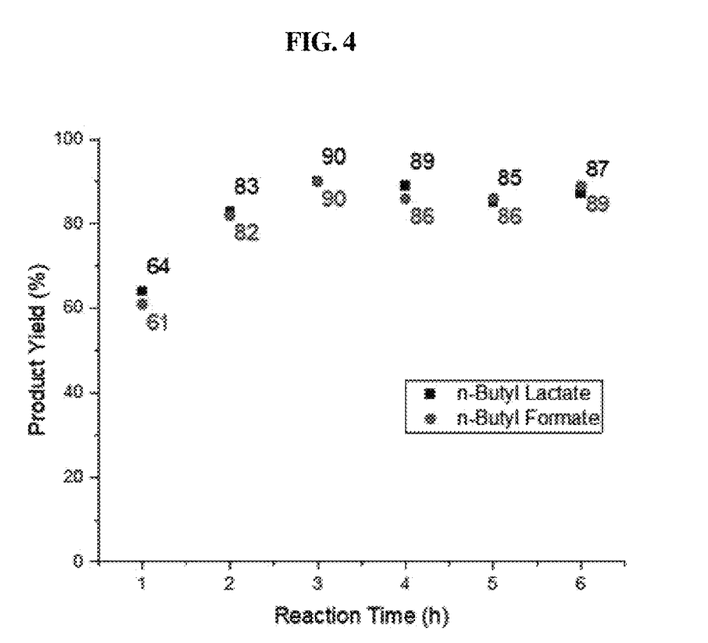
FIG. 4 is a graph showing the yield of butyl lactate and butyl formate at a reaction temperature of 160° C. versus reaction time.
Figure 5:
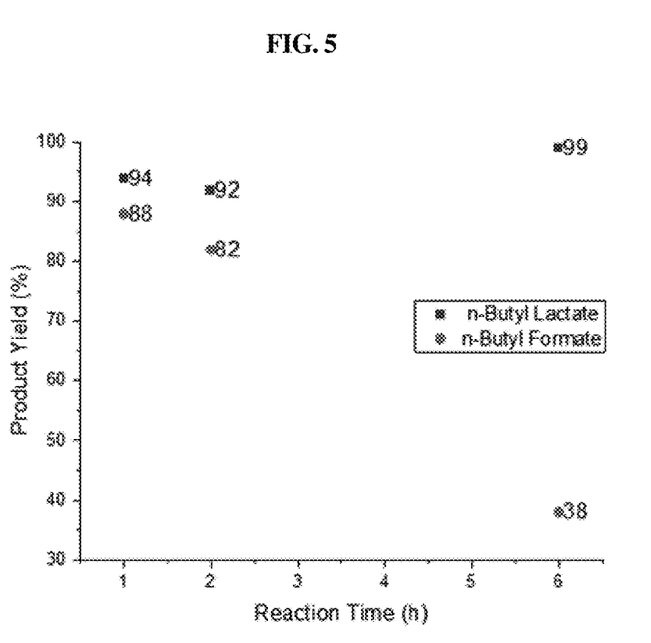
FIG. 5 is a graph showing the yield of butyl lactate and butyl formate at a reaction temperature of 180° C. versus reaction time.

In Examples 5 and 7 to 11 above, experiments were performed at 160° C. at different reaction time, and are shown in FIG. 4. Examples 6, 12, and 13 are the results of experiments performed at 180° C. at different reaction time and are shown in FIG. 5.

It was found that at 160° C., the reaction yield increased until the reaction time reached 3 hours, but at 180° C., the reaction was almost completed already within 1 hour. Rather, the yield of butyl formate at 180° C. tended to decrease with an increase in the reaction time, indicating that formate is unstable at high temperatures, thereby causing decomposition easily. Meanwhile, butyl lactate has the highest yield after 6 hours of reaction at 180° C., indicating that the yield of a desired product may be maximized through appropriate control of the reaction temperature and reaction time.

<Roles of Formate as Trialkylphosphate-Based Solvent and Reactant>

Compared to Comparative Examples 5 and 6, it was found that when tributyl phosphate (TBP) was added, the yield of the esterification reaction greatly increased. That indicates that through the carbonation reaction, lactic acid or formic acid is produced, and due to their hydrophilicity, lactic acid or formic acid is distributed in a higher concentration in an aqueous phase than in an organic phase formed of alcohol, and when exposed to high temperatures, the rate of the polymerization reaction generating oligomers, which are side reactions, may greatly increase compared to the rate of the esterification reaction, but the lactic acid produced with the addition of tributyl phosphate may be induced to be uniformly dispersed in the overall reaction medium. Meanwhile, the resulting alkyl derivatives of lactic acid and formic acid serve as amphoteric materials to facilitate mass transfer at a phase interface, allowing carbonation, and the acidity of the reaction medium to be kept in acidic levels, and thus, a decrease in yield due to side reactions or reverse reactions (hydrolysis) that may be shown during esterification reaction is greatly suppressed.

As another comparison for describing the effect thereof, the esterification reaction in the case where a hydrophobic solvent replaced tributyl phosphate (Comparative Example 7) and the case that tributyl phosphate was not replaced (Example 6) may be observed. Dodecane, a solvent used in Comparative Example 7, is an alkane-based solvent and is known to distribute lactic acid present in an aqueous solution relatively well. However, it is found that water produced during the reaction and dodecane having extreme hydrophobicity cause a continuous unstable phase, and as lactic acid concentrated in the aqueous solution forms oligomers at a relatively higher rate, the product yield of the esterification reaction is quite low.

Meanwhile, when comparing Comparative Example 6 having only lactate without formate as an object of the esterification reaction with Example 13 having lactate and formate together, the yield of butyl lactate greatly increased to 99% (Example 10) from 89% (Comparative Example 3), and even in Examples 12 and 6 having shorter reaction time, the yield of butyl lactate was shown to be higher than that of Comparative Example 6.

Against this backdrop, it is believed that the simultaneous esterification of the reactants in which lactate and formic acid are present together allows an overall esterification yield to be kept high than the esterification of reactants containing lactate alone.

While the present disclosure is described with reference to accompanying drawings, this is intended to be illustrative, and it will be understood by those of ordinary skill in the art that various modifications and equivalent arrangements may be made therein. Hence, the protective scope of the present disclosure shall be determined by the scope of the appended claims.

What is claimed is:

1. A method of converting carbon dioxide to formic acid, comprising:
    reacting at least one among carbon dioxide and/or carbon dioxide-derived inorganic carbonate with hydrocarbon containing at least one hydroxyl group, in presence of a catalyst in which, as active metals in a catalyst complex, at least one of noble metals in Group VIII other than palladium (Pd) and at least one selected from among transition metals in Group VIII other than the noble metals and palladium (Pd) are supported on a support.

2. The method of claim 1, wherein the noble metals are at least one selected from among ruthenium (Ru), iridium (Ir), rhodium (Rh), and platinum (Pt).

3. The method of claim 1, wherein the transition metals other than the noble metals in the catalyst complex comprise at least one selected from among nickel (Ni), iron (Fe), and cobalt (Co).

4. The method of claim 1, wherein the support is at least one selected from among a carbonaceous material, a molecular sieve, a ceramic material, and a metal oxide.

5. The method of claim 1, wherein the hydrocarbon containing at least one hydroxyl group is one selected from among a monohydric alcohol and a polyhydric alcohol, or a mixture thereof.

6. The method of claim 5, wherein the hydrocarbon containing at least one hydroxyl group is one selected from among glucose, mannose, galactose, xylose, sorbitol, mannitol, galactitol, xylitol, glycerol, 1,4-butanediol or an isomer thereof, 1,4-pentanediol or an isomer thereof, 1,2-propanediol or an isomer thereof, butanol, pentanol, and propanol, or a mixture thereof.

7. The method of claim 6, wherein the hydrocarbon containing at least one hydroxyl group is glycerol and/or glucose.

8. The method of claim 1, wherein the reacting is performed at a temperature of 180° C. to 240° C.

9. The method of claim 1, further comprising, before reacting the hydrocarbon containing at least one hydroxyl group with the inorganic carbonate, reacting the carbon dioxide with at least one selected from among a metal, a metal salt, and an ammonium salt to produce the inorganic carbonate.

10. A process for simultaneously converting carbon dioxide-derived metal carbonate and glycerol, comprising:
    a) performing, in the presence of a catalyst complex for carbon dioxide conversion reaction, a simultaneous conversion reaction of a carbon dioxide-derived metal carbonate and glycerol to obtain a reaction product;
    b) forming a mixture in which at least one selected from among $C_4$ to $C_8$ alcohols and trialkyl phosphate (TAP) are added to the obtained reaction product;
    c) removing some moisture from the mixed solution;
    d) performing carbonation and esterification by adding carbon dioxide ($CO_2$) to the mixed solution from which some moisture is removed, and performing an esterification reaction to synthesize alkyl lactate and alkyl formate;
    e) separating the alkyl lactate and the alkyl formate produced in step d) from each other through a conventional distillation method; and
    f) recovering the metal carbonate produced as a reaction by-product in step d), and recycling the metal carbonate to the simultaneous conversion reaction of glycerol and metal carbonate,
    wherein the catalyst complex is a catalyst in which at least one of noble metals and at least one selected from among transition metals other than the noble metals are supported as an active metal on a support.

11. The process of claim 10, wherein an amount of the alcohol added in step b) is 1 to 50 in a ratio of the number of moles to a sum of the number of moles of metal lactate and metal formate, and a molar ratio of the alcohol to trialkyl phosphate (TBP) is 1:5 to 5:1.

12. The process of claim 10, wherein the carbon dioxide added in step d) is supplied while being pressurized in a range of atmospheric pressure to 60 bar.

13. The process of claim 10, wherein the carbonation and esterification processes in step d) are performed in a temperature range of 120° C. to 200° C.

14. The process of claim 10, wherein at least one alcohol selected from among $C_4$ to $C_8$ added in step b) is butanol, and an inert organic solvent is tributyl phosphate (TBP).

15. The process of claim 10, further comprising g) hydrolyzing the alkyl lactate and the alkyl formate to produce a lactic acid and a formic acid.

16. The process of claim 10, wherein the trialkyl phosphate (TAP) is added in step d) after the removing of moisture, instead of being added in step b).

* * * * *